United States Patent [19]
Shibata et al.

[11] Patent Number: 4,564,643
[45] Date of Patent: Jan. 14, 1986

[54] PROCESS FOR THE PRODUCTION OF MIXED ALCOHOLS

[75] Inventors: Masatoshi Shibata; Soichi Uchiyama; Yoshinobu Aoki, all of Chiba, Japan

[73] Assignee: Research Association for Petroleum Alternatives Development, Tokyo, Japan

[21] Appl. No.: 731,750

[22] Filed: May 7, 1985

Related U.S. Application Data

[63] Continuation of Ser. No. 551,330, Nov. 14, 1983, abandoned.

[30] Foreign Application Priority Data

Dec. 29, 1982 [JP]  Japan ............................. 57-229834

[51] Int. Cl.[4] ...................... C07C 27/06; C07C 31/04
[52] U.S. Cl. .................................. 518/717; 518/714; 518/719; 518/721
[58] Field of Search ................................ 518/717, 714

[56] References Cited

U.S. PATENT DOCUMENTS 1,963,119  6/1934  Dreyfus ............................. 518/714
1,996,101  4/1935  Dreyfus ............................. 518/714

FOREIGN PATENT DOCUMENTS 2118061  10/1983  United Kingdom ................ 518/717

Primary Examiner—Howard T. Mars
Attorney, Agent, or Firm—Frishauf, Holtz, Goodman & Woodward

[57] ABSTRACT

A process for producing a mixed alcohol by contacting a synthesis gas with a catalyst, wherein the catalyst is a solid substance prepared by:

calcining a mixture of (A) a zinc compound, (B) a compound of at least one metal selected from iron, cobalt, and nickel, and (C) a compound of at least one metal selected from the metals belonging to Groups II–VII of the Periodic Table;

impregnating the above-calcined product with (D) an alkali metal compound and/or an alkaline earth metal compound;

calcining the resulting mixture; and reducing the thus-calcined product.

The selectivity of the mixed alcohol is high in the process of the present invention. This is one of the advantages of the present invention. Furthermore, the proportion of alcohols other than methanol in the mixed alcohol is relatively high, and thus the mixed alcohol is suitable for use as an alcohol component to be compounded to gasoline.

8 Claims, No Drawings

PROCESS FOR THE PRODUCTION OF MIXED ALCOHOLS

This application is a continuation of application Ser. No. 551,330 filed Nov. 14, 1983 now abandoned.

BACKGROUND OF THE INVENTION

In view of a rise in price of gasoline for cars due to the aggravation of oil situation, an attempt to produce inexpensive car fuel by adding mixed alcohols to gasoline have been made in recent years. The reason why mixed alcohols are used as an alcohol component to be added to gasoline is that if methanol alone is added to gasoline, it combines together with water in gasoline to form a water/methanol mixture, resulting in the formation of two layers, i.e., a gasoline layer and a water/methanol mixed layer, in a storage tank.

Various methods of producing such mixed alcohols have been proposed. Japanese Patent Application Laid-Open No. 7727/1981, for example, discloses a process for producing mixed alcohols from synthesis gas by the use of a rhodium-base catalyst. This process, however, is not preferred in that large amounts of by-products such as acetic acid and aldehyde result. In addition, as catalysts for use in the production of mixed alcohols from synthesis gas, a ruthenium-base catalyst (Japanese Patent Application Laid-Open No. 82327/1982), alkali metal-modified ones of a zinc-chromium catalyst and a copper-zinc catalyst (Japanese Patent Application Laid-Open No. 10689/1982), and a copper-cobalt catalyst (Japanese Patent Application Laid-Open No. 85530/1980) are known. Methods utilizing these catalysts, however, should be performed under elevated pressures. This will need expensive equipment and cause many side reactions. Hence they cannot be said to be advantageous for practical use.

SUMMARY OF THE INVENTION

The present invention is intended to overcome the above-described problems of conventional methods, and an object of the invention is to provide a process for producing mixed alcohols from synthesis gas with efficiency under relatively low pressures.

The present invention relates to a process for producing a mixed alcohol comprising methanol and higher alcohols than methanol by contacting synthesis gas with a catalyst, wherein the catalyst is a solid substance prepared by:
calcining a mixture of (A) a zinc compound, (B) a compound of at least one metal selected from iron, cobalt, and nickel, and (C) a compound of at least one metal selected from the metals belonging to Groups II, III and IV and the fourth period of Groups V, VI and VII of the Periodic Table;
impregnating the above-calcined product with (D) an alkali metal compound and/or an alkaline earth metal compound;
calcining the resulting mixture; and
reducing the thus-calcined product.

DETAILED DESCRIPTION OF THE INVENTION

A method of preparing the catalyst of the invention will hereinafter be explained in detail.

As Compound (A), any suitable compound containing zinc can be used. Usually water-soluble compounds are preferred. Suitable examples of zinc compounds include zinc nitrate, zinc sulfate, and zinc chloride.

Compound (B) is a compound containing at least one of iron, cobalt, and nickel. Particularly preferred are water-soluble compounds. Suitable examples are the nitrates, sulfates, and chlorides of the metals.

Compound (C) is a compound of at least one metal selected from the metals belonging to Groups II, III and IV, and the fourth period of Groups V, VI and VII of the Periodic Table. Typical examples of the metals belonging to Groups II, III and IV of the Periodic Table are magnesium, calcium, boron, aluminum, gallium, lanthanum, silicon, germanium, titanium, tin, and zirconium. Suitable examples of the metals belonging to the fourth period of Groups V, VI and VII of the Periodic Table are vanadium, chromium, and manganese. As Compound (C), various compounds of the metals as described above, such as the nitrates, sulfates, chlorides, and oxides thereof, can be used. Particularly preferred are water-soluble compounds.

In the preparation of the catalyst of the invention, Compounds (A), (B) and (C) are first mixed and calcined.

Compounds (A), (B) and (C) can be mixed by techniques such as a co-precipitation method, a kneading method, and a dipping method. In accordance with the co-precipitation method, for example, they are added to water to form aqueous solutions or suspensions, which are then mixed and co-precipitated by adjusting the pH through addition of a co-precipitating agent such as sodium carbonate, sodium hydroxide, and potassium hydroxide at room temperature or at elevated temperatures. Then, the resulting precipitate is aged, if necessary, and washed with water, dried and calcined at a temperature of from 200° to 500° C.

The above-calcinated product is then impregnated with Compound (D), i.e., an alkali metal compound and/or an alkaline earth metal compound. Compound (D) is preferably water-soluble. Suitable examples include sodium carbonate and magnesium acetate. In the impregnation of the calcined product, Compound (D) is used as an aqueous solution; that is, the calcined product is impregnated with an aqueous solution of Compound (D). After the process of impregnation, the resulting mixture should be calcined again. This calcination is usually performed at a temperature of from 100° to 500° C.

It is necessary for the composition of the thus-calcined product to be controlled so that the amount of Compound (A) is from 5 to 70% by weight, the amount of Compound (B) is from 1 to 50% by weight, the amount of Compound (C) is from 1 to 70% by weight, and the amount of Compound (D) is from 0.1 to 15% by weight (calculated as oxide, respectively).

The calcined product is then reduced. This reduction is sufficient to be performed at a temperature of from 200° to 400° C. by the use of a reducing atmosphere, for example, in the presence of hydrogen or carbon monoxide.

The thus-prepared solid substance is used as the catalyst of the invention.

Although Compounds (A), (B), (C) and (D) can be mixed and calcined simultaneously, Compound (D) of alkali or alkaline earth metal compound is dispersed only insufficiently and unevenly in the final product by such a procedure. Hence this procedure fails to produce the desired catalyst.

In the process of the invention, the solid substance as prepared above is used as a catalyst, and synthesis gas, i.e., a mixed gas of hydrogen and carbon monoxide, is contacted with the catalyst to produce a mixed alcohol. The composition of the synthesis gas to be used as a feed in the process of the invention is not critical. In general, however, it is preferred to use synthesis gas in which the molar ratio of hydrogen to carbon monoxide is within the range of from 1:3 to 3:1.

Other reaction conditions for the process of the invention are not critical and can be determined appropriately. The reaction temperature is usually from 200° to 550° C. and preferably from 240° to 450° C.; the reaction pressure may be relatively low, in general, ranges between 20 and 200 kilograms per square centimeter (by gauge) and preferably between 40 and 60 kilograms per square centimeter (by gauge); and the gas hourly space velocity (GHSV) is from 500 to 100,000 per hour and preferably from 1,000 to 50,000 per hour.

The process of the invention as described above produces mixed alcohols comprising methanol and higher alcohols than methanol, such as ethanol, propanol, and butanol, and other compounds such as aldehydes and esters. The selectivity of the mixed alcohol is high in the process of the invention. This is one of the advantages of the present invention. Another advantage is that the costs of equipment and operation, for example, can be greatly reduced, since the reaction pressure in the process of the invention is sufficient to be relatively low. Furthermore the proportion of alcohols other than methanol in the mixed alcohol as produced by the process of the invention is relatively high, and thus the mixed alcohol is suitable for use as an alcohol component to be compounded to gasoline.

The present invention is described in greater detail with reference to the following examples.

EXAMPLE 1

An aqueous solution (2.5 liters) containing 59.5 grams of zinc nitrate (6 hydrate), 29.1 grams of cobalt nitrate (6 hydrate), and 25.6 grams of magnesium nitrate was prepared and heated to 60° C. Separately 2.5 liters of an aqueous solution containing 88.3 grams of sodium carbonate (anhydrous) as a co-precipitating agent was prepared and heated to 60° C. These aqueous solutions were mixed rapidly and, after completion of precipitation, aged. Then the resulting mixture was filtered, and the precipitate thus obtained was washed sufficiently with water.

The thus-obtained co-precipitate was dried at 120° C. for about 12 hours and then calcined at 450° C. for 2 hours.

The thus-calcined product was impregnated with an aqueous solution containing 3.4 grams of sodium carbonate (anhydrous) and then dried at 120° C. for about 12 hours. Then graphite was added, and the resulting mixture was pelletized and pulverized to form 16–32 mesh grains. This catalyst precursor had a composition of Zn:Co:Mg:Na=0.43:0.22:0.22:0.13 (molar ratio).

Then 1 milliliter of the catalyst precursor was packed in a reaction tube of stainless steel. While passing a 1:9 (molar ratio) mixture of carbon monoxide and nitrogen as a reducing gas through the reaction tube at a gas hourly space velocity (GHSV) of 4,000 per hour, the catalyst precursor was gradually heated and reduced at 240° C. for 12 hours to produce a catalyst.

A synthesis gas (carbon monoxide:hydrogen=1:2 (molar ratio)) was introduced into the reaction tube at a gas hourly space velocity (GHSV) of 4,000 per hour. The pressure was increased to 50 kilograms per square centimeter (by gauge). Then the temperature was increased to a reaction temperature at which the conversion of carbon monoxide (excluding the one converted into carbon dioxide) reached about 20%.

The reaction products were introduced, without being condensed at the outlet of the reaction tube, through a tube maintained at 200° C. into a gas chromatography instrument where they were analyzed. The column filler as used in this gas chromatography analysis was a mixture of activated carbon, Porapak-Q (produced by Water Co.), and Porapak-N (produced by Water Co.).

The results are shown in Table 1.

EXAMPLE 2

The procedure of Example 1 was repeated wherein the preparation of the catalyst was performed using the following compounds:

| | |
|---|---|
| zinc nitrate (6 hydrate) | 59.5 grams |
| cobalt nitrate (6 hydrate) | 29.1 grams |
| aluminum nitrate (9 hydrate) | 75.0 grams |
| sodium carbonate (anhydrous) (co-precipitating agent) | 90.2 grams |
| sodium carbonate (anhydrous) (for impregnation) | 3.4 grams |

Composition of catalyst precursor:

Zn:Co:Al:Na=0.36:0.18:0.36:0.10 (molar ratio)

The results are shown in Table 1.

EXAMPLE 3

The procedure of Example 1 was repeated wherein the preparation of the catalyst was performed using the following compounds:

| | |
|---|---|
| zinc nitrate (6 hydrate) | 59.5 grams |
| cobalt nitrate (6 hydrate) | 29.1 grams |
| aluminum nitrate (9 hydrate) | 75.0 grams |
| sodium carbonate (anhydrous) (for co-precipitation) | 90.2 grams |
| magnesium acetate (4 hydrate) | 13.7 grams |

Composition of catalyst precursor:

Zn:Co:Al:Mg=0.36:0.18:0.36:0.10 (molar ratio)

The results are shown in Table 1.

EXAMPLE 4

The procedure of Example 1 was repeated wherein the preparation of the catalyst was performed using the following compounds:

| | |
|---|---|
| zinc nitrate (6 hydrate) | 59.5 grams |
| cobalt nitrate (6 hydrate) | 29.1 grams |
| gallium nitrate (8 hydrate) | 79.9 grams |
| sodium carbonate (anhydrous) (for co-precipitation) | 89.2 grams |
| sodium carbonate (anhydrous) (for impregnation) | 3.4 grams |

Composition of catalyst precursor:

Zn:Co:Ga:Na=0.36:0.18:0.36:0.10 (molar ratio)

The results are shown in Table 1.

EXAMPLE 5

The procedure of Example 1 was repeated wherein the preparation of the catalyst was performed using the following compounds:

| | |
|---|---|
| zinc nitrate (6 hydrate) | 59.5 grams |
| cobalt nitrate (6 hydrate) | 29.1 grams |
| water glass (SiO$_2$ content: 28.6% by weight) | 61.7 grams |
| sodium carbonate (anhydrous) (for co-precipitation) | 35.3 grams |
| sodium carbonate (anhydrous) (for impregnation) | 3.4 grams |

Composition of catalyst precursor:

Zn:Co:Si:Na=0.36:0.18:0.36:0.10 (molar ratio)

The results are shown in Table 1.

EXAMPLE 6

The procedure of Example 1 was repeated wherein the preparation of the catalyst was performed using the following compounds:

| | |
|---|---|
| zinc nitrate (6 hydrate) | 59.5 grams |
| cobalt nitrate (6 hydrate) | 29.1 grams |
| zirconium oxychloride (8 hydrate) | 64.4 grams |
| sodium carbonate (anhydrous) (for co-precipitation) | 63.8 grams |
| potassium carbonate (anydrous) (for impregnation) | 4.2 grams |

Composition of catalyst precursor:

Zn:Co:Zr:K=0.36:0.18:0.36:0.10 (molar ratio)

The results are shown in Table 1.

EXAMPLE 7

The procedure of Example 1 was repeated wherein the preparation of the catalyst was performed using the following compounds:

| | |
|---|---|
| zinc nitrate (6 hydrate) | 59.5 grams |
| cobalt nitrate (6 hydrate) | 29.1 grams |
| chromium nitrate (9 hydrate) | 80.0 grams |
| sodium carbonate (anhydrous) (for co-precipitation) | 92.5 grams |
| sodium carbonate (anhydrous) (for impregnation) | 3.4 grams |

Composition of catalyst precursor:

Zn:Co:Cr:Na=0.36:0.18:0.36:0.10 (molar ratio)

The results are shown in Table 1.

EXAMPLE 8

The procedure of Example 1 was repeated wherein the preparation of the catalyst was performed using the following compounds:

| | |
|---|---|
| zinc nitrate (6 hydrate) | 59.5 grams |
| cobalt nitrate (6 hydrate) | 29.1 grams |
| lanthanum nitrate (6 hydrate) | 86.6 grams |
| sodium carbonate (anhydrous) (for co-precipitation) | 74.2 grams |
| magnesium acetate (4 hydrate) | 13.7 grams |

Composition of catalyst precursor:

Zn:Co:La:Mg=0.36:0.18:0.36:0.10 (molar ratio)

The results are shown in Table 1.

EXAMPLE 9

The procedure of Example 1 was repeated wherein the preparation of the catalyst was performed using the following compounds:

| | |
|---|---|
| zinc nitrate (6 hydrate) | 59.5 grams |
| nickel nitrate (6 hydrate) | 29.1 grams |
| aluminum nitrate (9 hydrate) | 75.0 grams |
| sodium carbonate (anhydrous) (for co-precipitation) | 81.3 grams |
| potassium carbonate (anhydrous) (for impregnation) | 4.2 grams |

Composition of catalyst precursor:

Zn:Ni:Al:Na=0.36:0.18:0.36:0.10 (molar ratio)

The results are shown in Table 1.

EXAMPLE 10

The procedure of Example 1 was repeated wherein the preparation of the catalyst was performed using the following compounds:

| | |
|---|---|
| zinc nitrate (6 hydrate) | 59.5 grams |
| nickel nitrate (6 hydrate) | 29.1 grams |
| zirconium oxychloride (8 hydrate) | 64.4 grams |
| sodium carbonate (anhydrous) (for co-precipitation) | 70.7 grams |
| potassium carbonate (anhydrous) (for impregnation) | 4.2 grams |

Composition of catalyst precursor:

Zn:Ni:Zr:Na=0.36:0.18:0.36:0.10 (molar ratio)

The results are shown in Table 1.

EXAMPLE 11

The procedure of Example 1 was repeated wherein the preparation of the catalyst was performed using the following compounds:

| | |
|---|---|
| zinc nitrate (6 hydrate) | 59.5 grams |
| nickel nitrate (6 hydrate) | 29.1 grams |
| Aqueous titanium sulfate solution (Ti(SO$_4$)$_2$ content: 29.8% by weight) | 161.1 grams |
| sodium carbonate (anhydrous) (for co-precipitation) | 133.0 grams |

(After co-precipitation followed by filtration, the resulting co-precipitate was washed with water and further with an aqueous solution of NaCl (0.5 mole per liter) to remove SO$_4^{2-}$).

| | |
|---|---|
| sodium carbonate (anhydrous) (for impregnation) | 4.2 grams |

Composition of catalyst precursor:

Zn:Ni:Ti:Na=0.34:0.17:0.34:0.15 (molar ratio)

The results are shown in Table 1.

EXAMPLE 12

The procedure of Example 1 was repeated wherein the preparation of the catalyst was performed using the following compounds:

| | |
|---|---|
| zinc nitrate (6 hydrate) | 59.5 grams |
| iron nitrate (9 hydrate) | 40.4 grams |
| aluminum nitrate (9 hydrate) | 75.0 grams |
| sodium carbonate (anhydrous) (for co-precipitation) | 93.4 grams |
| sodium carbonate (anhydrous) (for impregnation) | 3.4 grams |

Composition of catalyst precursor:

Zn:Fe:Al:Na=0.36:0.18:0.36:0.10 (molar ratio)

The results are shown in Table 1.

EXAMPLE 13

The procedure of Example 1 was repeated wherein the preparation of the catalyst was performed using the following compounds:

| | |
|---|---|
| zinc nitrate (6 hydrate) | 59.5 grams |
| iron nitrate (9 hydrate) | 40.4 grams |
| zirconium oxychloride (8 hydrate) | 64.4 grams |
| sodium carbonate (anhydrous) (for co-precipitation) | 89.3 grams |
| sodium carbonate (anhydrous) (for impregnation) | 3.4 grams |

Composition of catalyst precursor:

Zn:Fe:Zr:Na=0.36:0.18:0.36:0.10 (molar ratio)

The results are shown in Table 1.

What is claimed is:

1. In a process for producing a mixed alcohol comprising methanol and higher alcohols than methanol comprising contacting a synthesis gas with a catalyst whereby methanol and higher alcohols are formed and recovered,
   the improvement comprising using as said catalyst, a solid catalyst prepared by
   calcining a mixture consisting essentially of (A) from 5 to 70% by weight, calculated as oxide, of a zinc compound, (B) from 1 to 50% of a nickel compound, and (C) from 1 to 70% of an aluminum compound or of a zirconium compound to form a calcined product;
   impregnating said calcined product with (D) from 0.1 to 15% of an alkali metal compound;
   calcining said calcined product impregnated with said alkali metal compound to form an alkali metal-containing calcined product; and
   reducing said alkali metal-containing calcined product to form said catalyst.

2. The process for the production of mixed alcohols as claimed in claim 1, wherein said component (C) is an aluminum compound.

3. The process for the production of mixed alcohols as claimed in claim 1, wherein said component (C) is a zirconium compound.

4. The process for the production of mixed alcohols as claimed in claim 1, wherein the Compound (D) is a compound of at least one metal selected from the group consisting of sodium and potassium.

5. The process for the production of mixed alcohols as claimed in claim 1, wherein the Compound (C) is aluminum compound and the Compound (D) is sodium compound.

6. The process for the production of mixed alcohols as claimed in claim 1, wherein the Compound (C) is zirconium compound and the Compound (D) is potassium compound.

7. The process for the production of mixed alcohols as claimed in claim 1, wherein the Compound (C) is aluminum compound and the Compound (D) is potassium compound.

8. The process for the production of mixed alcohols as claimed in claim 1, wherein the Compound (C) is zirconium compound and the Compound (D) is sodium compound.

* * * * *

TABLE 1

| Example | Composition of Catalyst Precursor (molar ratio) | Reaction Temperature (°C.) | Conversion of Carbon Monoxide*1 (%) | Selectivity of Alcohol*2 (%) | Composition of Mixed Alcohol (% by weight) | | | |
|---|---|---|---|---|---|---|---|---|
| | | | | | Methanol | Ethanol | Propanol | Butanol and Higher Alcohols than Butanol |
| 1 | Zn.Co$_{0.5}$.Mg.Na$_{0.3}$ | 288 | 20 | 47 | 54 | 28 | 10 | 8 |
| 2 | Zn.Co$_{0.5}$.Al.Na$_{0.3}$ | 310 | 20 | 56 | 50 | 31 | 11 | 8 |
| 3 | Zn.Co$_{0.5}$.Al.Mg$_{0.3}$ | 334 | 19 | 53 | 70 | 22 | 5 | 3 |
| 4 | Zn.Co$_{0.5}$.Ga.Na$_{0.3}$ | 312 | 21 | 54 | 52 | 30 | 11 | 7 |
| 5 | Zn.Co$_{0.5}$.Si.Na$_{0.3}$ | 320 | 22 | 50 | 51 | 29 | 12 | 8 |
| 6 | Zn.Co$_{0.5}$.Zr.K$_{0.3}$ | 288 | 20 | 42 | 45 | 31 | 11 | 3 |
| 7 | Zn.Co$_{0.5}$.Cr.Na$_{0.3}$ | 335 | 20 | 62 | 72 | 20 | 6 | 2 |
| 8 | Zn.Co$_{0.5}$.La.Mg$_{0.3}$ | 306 | 20 | 41 | 45 | 28 | 18 | 9 |
| 9 | Zn.Ni$_{0.5}$.Al.K$_{0.3}$ | 388 | 18 | 58 | 46 | 19 | 28 | 7 |
| 10 | Zn.Ni$_{0.5}$.Zr.K$_{0.3}$ | 367 | 19 | 64 | 50 | 25 | 20 | 5 |
| 11 | Zn.Ni$_{0.5}$.Ti.Na$_{0.4}$ | 360 | 21 | 65 | 75 | 14 | 8 | 3 |
| 12 | Zn.Fe$_{0.5}$.Al.Na$_{0.3}$ | 280 | 22 | 49 | 49 | 31 | 12 | 8 |
| 13 | Zn.Fe$_{0.5}$.Zr.Na$_{0.3}$ | 282 | 21 | 48 | 45 | 34 | 13 | 8 |

Note:

*1 Conversion of Carbon Monoxide = $\dfrac{\text{Amount of Carbon Monoxide Converted into Alcohol (moles)} - \text{Amount of Carbon Dioxide Formed (moles)}}{\text{Amount of Carbon Monoxide Introduced (moles)}} \times 100$

*2 Selectivity of Alcohol = $\dfrac{\text{Amount of Carbon Monoxide Converted into Alcohol (moles)}}{\text{Amount of Carbon Monoxide Converted (moles)} - \text{Amount of Carbon Dioxide Formed (moles)}} \times 100$